United States Patent [19]
Goble et al.

[11] Patent Number: 5,423,810
[45] Date of Patent: Jun. 13, 1995

[54] CAUTERISING APPARATUS

[75] Inventors: Nigel M. Goble, Nr. Cardiff; Colin C. O. Goble, Cardiff, both of United Kingdom

[73] Assignee: G2 Design Limited, Cardiff, United Kingdom

[21] Appl. No.: 22,178

[22] Filed: Feb. 25, 1993

[30] Foreign Application Priority Data

Feb. 27, 1992 [GB] United Kingdom ............... 9204217

[51] Int. Cl.⁶ .................................... A61B 17/39
[52] U.S. Cl. ................................ 606/40; 606/38
[58] Field of Search ............................ 606/38-40

[56] References Cited

U.S. PATENT DOCUMENTS

| | | | |
|---|---|---|---|
| 4,474,179 | 10/1984 | Koch | 606/38 |
| 4,691,703 | 9/1987 | Auth et al. | 128/303.1 |
| 5,167,658 | 12/1992 | Ensslin | 606/38 |
| 5,167,660 | 12/1992 | Altendorf | 606/40 |

FOREIGN PATENT DOCUMENTS

| | | | |
|---|---|---|---|
| 0136855 | 4/1985 | European Pat. Off. | 606/38 |
| 0448798 | 12/1990 | European Pat. Off. | |
| 2502935 | 10/1982 | France | 606/40 |
| 627757 | 3/1936 | Germany | |
| 3120102 | 12/1982 | Germany | |
| 3830193 | 3/1990 | Germany | |
| 2213381 | 8/1985 | United Kingdom | 606/38 |
| 2214430 | 9/1989 | United Kingdom | |
| 91/16859 | 11/1991 | WIPO | |

*Primary Examiner*—Lee S. Cohen
*Attorney, Agent, or Firm*—Fish & Richardson

[57] ABSTRACT

Electrosurgical cauterising apparatus has a radio frequency generator with a power oscillator which generates a bipolar cauterising output signal for application to a pair of cauterising electrodes. The oscillator carrier frequency varies according to the load resistance represented by tissue being cauterised and this variation is used to monitor the tissue resistance as cauterisation progresses. The apparatus generates a cauterisation termination signal according to progress of the tissue resistance on a resistance versus time curve characteristic of the tissue cauterisation process.

19 Claims, 2 Drawing Sheets

CAUTERISING APPARATUS

This invention relates to electrosurgical cauterising apparatus for use in surgery.

BACKGROUND OF THE INVENTION

One of the most important electrosurgical operations is in cautery. Cautery is best performed using bipolar electrosurgical apparatus. Two active electrodes forming, for example, the tips of a pair of forceps, are used to grasp a cut blood vessel. Pressure is applied to the forceps to close the vessel, and radio frequency (RF) power is applied to the electrodes to seal the vessel. In electrosurgical cauterisation, the optimum amount of RF power is that which is the minimum which causes the blood vessel to be sealed.

It is current practice for both the level and duration of application of RF power to be controlled by the operator. Different surgeons tend to use different power settings and different coagulation end-points. There are no standards relating to the power-time envelope that should be used on a particular size of blood vessel, and consequently optimum levels of electrosurgical energy are rarely used in practice. Generally, it is the colour of the cauterised vessel which is used by the operator to judge when the right degree of cauterisation has been achieved. Some operators choose to cauterise to an off-white colour whereas others prefer to cauterise to the extent that the vessel is blackened. In both cases the speed of cautery is limited by the reaction time of the operator in switching the RF power source off. This factor also limits the maximum amount of RF power which may be applied, since the coagulation end-point depends on both the period of power application and the power level. The higher the power level, the faster the colour of the vessel changes and the more difficult it is to achieve the optimum degree of cauterisation.

SUMMARY OF THE INVENTION

The applicants have found that when a blood vessel is cauterised between a pair of active electrodes, its electrical resistance, as measured across the electrodes, varies widely. When power is first applied, the vessel has a low resistance due to its electrolyte content in solution. As the vessel heats up, the impedance becomes lower still, principally because the temperature coefficient of electrical conductivity for dissolved sodium chloride is positive (in the region of 2% per degree C.). A next stage is boiling off the water content of the vessel. At this point the impedance momentarily reduces further as the ionic components become more concentrated, but then the vessel begins to become desiccated and the impedance increases rapidly. Subsequently, the vessel begins to carbonise and the impedance drops again to a low value. Typically, the changes in the impedance of the blood vessel are in the region of 10Ω to 1kΩ. It will be appreciated that, with the non-linear power/load curve for a typical RF generator, this variation in impedance also causes considerable changes in the absorbed power as the impedance presented to the generator enters and leaves the range of matched impedances. This narrow load impedance matching characteristic of most RF generators limits the choice of power level and the duration of power application, and contributes to the difficulty in achieving optimum cauterisation. Since in major surgery the cautery of blood vessels can present a significant proportion of an operation, with vessels being difficult to grasp and difficult to see, particularly with the current trend towards minimally invasive surgery, there is a pressing need for faster and more accurate cautery.

According to one aspect of the present invention, we provide electrosurgical cauterising apparatus having the ability to sense changes in a property of the tissue being cauterised at the site of application of electrosurgical energy, and means for automatically controlling the RF power level and/or the time of application in response to a sensed change. The property is preferably the electrical resistance of the tissue during cautery. The apparatus may comprise a cauterising tool having a pair of electrodes coupled to respective output terminals of a radio frequency power generator, wherein the generator includes means for monitoring the change in electrical resistance between the electrodes due to cauterisation, and control means for controlling the application of radio frequency power to the electrodes in response to the monitoring means, to achieve a required degree of cauterisation. According to another aspect of the invention, a method of operating electrosurgical cauterising apparatus comprises applying a radio frequency cauterising voltage across a pair of electrodes of a cauterising tool, monitoring changes in a property of the tissue being cauterised during cautery, and controlling the application of the said voltage in response to the monitored changes to achieve a required degree of cauterisation.

Preferably, the monitoring means detects the fall in tissue resistance due to the initial heating of a blood vessel as well as the subsequent rise in resistance due to desiccation in order automatically to cut off the application of RF power to the electrodes at a predetermined point. Indeed, it is possible to incorporate in the apparatus a control for setting a desired level of cautery (i.e. according to whether the colour of the vessel at the end of the cauterisation operation is to be off-white or black or any intermediate colour) and to cut off RF power application at any of several corresponding points in the resistance/time graph. By using automatic electronic means to sense the level of cauterisation and to cut off the application of RF power, a response time of less than 1 ms can typically be achieved, as compared to a typical human reaction time of 200 ms. Consequently, the point of power cut-off is far more accurately determined. By continuous or repeated monitoring during the cauterisation process, it is also possible to adjust power level. The initial resistance of a blood vessel is directly proportional to the amount of power required to perform cautery, and therefore the initial power level can be adjusted automatically in each individual cauterising operation. Preferably, the apparatus is configured to sense the degree of cauterisation according to the ratio between the sensed resistance from time to time and this initially sensed resistance. Still greater definition of the point of cut-off is achieved by reducing the power level as the set end-point is reached.

In this way, decision-making about the cautery process is made far more quickly and accurately than with the conventional technique referred to above. Normal electrosurgical power levels no longer apply, since they were chosen to cater for human reaction time. Consequently, power levels may be increased by a factor of, for example, 10, but still with significant benefits in end-point determination. As a result of the characteristic resistance/time graph for the cauterisation of blood levels, the end-points can be determined consistently and repeatedly using apparatus in accordance with the invention. A blood vessel, regardless of size exhibits the same resistance changes throughout the cautery stages.

In the preferred embodiment of the invention, the RF power generator is so arranged that its output carrier frequency alters according to the load resistance. A generator having this characteristic is disclosed in our published U.S. Pat. No. 5,099,840, the contents of which are incorporated in this specification by reference. The resistance of the tissue being treated can therefore be monitored by monitoring the carrier frequency during cautery.

BRIEF DESCRIPTION OF THE DRAWINGS

The invention will now be described by way of example with reference to the drawings in which.

DESCRIPTION OF A PARTICULAR EMBODIMENT

Figure 1:
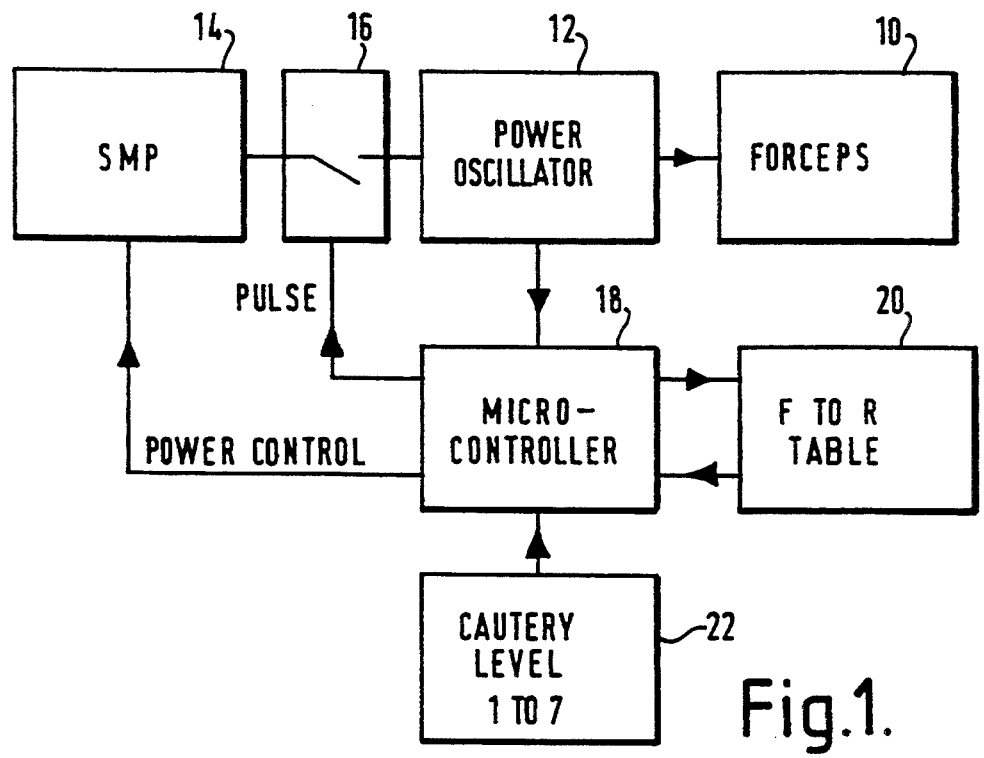
FIG. 1 is a block diagram of electrosurgical cauterisation apparatus in accordance with the invention.

Referring to FIG. 1, electrosurgical cauterising apparatus in accordance with the invention has a pair of forceps 10 coupled to the output of an RF generator which includes a power oscillator 12. The forceps may be of the construction shown in our co-pending patent application corresponding to European Patent Application, published as No. 0558318, and entitled "Surgical Apparatus for Bipolar Diathermy", the content of which is incorporated in this application by reference. The power oscillator 12 includes an automatic output impedance adjusting circuit as disclosed in our published U.S. Pat. No. 5,099,840, whereby the carrier frequency of the oscillator alters according to the resistance presented to it by the forceps load during cauterisation. The supply for the power oscillator 12 is derived from, in this embodiment, a switched mode power supply 14 via a switching device 16 for pulsing the oscillator. The power output of the oscillator 12 during each "on" period of the switching device 16 is controlled by altering the supply voltage available from the power supply 14.

Since the frequency of the oscillator 12 depends on the load resistance, measurement of the frequency can be used to measure the resistance. In this apparatus, the measurement is performed by a controller 18 including a microprocessor, in combination with a memory 20 containing a look-up table relating load resistance R to frequency F. Thus, during each "on" period of the power oscillator, the carrier frequency cycles are counted by the microcontroller 18, the count is fed as an address to the memory 20 which then writes the appropriate resistance value to the microcontroller 18, and according to software stored in the microcontroller 18, as well as the cautery level setting set in level-setting device 22, the oscillator is operated until a required level of cautery as determined by changes in load resistance is reached. Thus, the switching device 16 is repeatedly switched on to feed a serious of carrier bursts to the forceps until the required point on an resistance/time graph is attained.

In practice, it has been found that the ideal cauterising waveform is a modulated RF carrier in the frequency range 300 kHz to 5 MHz with a high crest factor (i.e. peak voltage/rms voltage). This is achieved by modulating the carrier using the switching device 16 to achieve a crest factor in the region of, for instance, 3 to 10, and preferably 9 to 10. Typically, the pulse repetition rate of the switching device 16 is between 10 kHz and 50 kHz. Accordingly, the operating carrier frequency is measured over a time window corresponding to an oscillator "on" time in the range of 2 to 100 $\mu s$.

Figure 2:
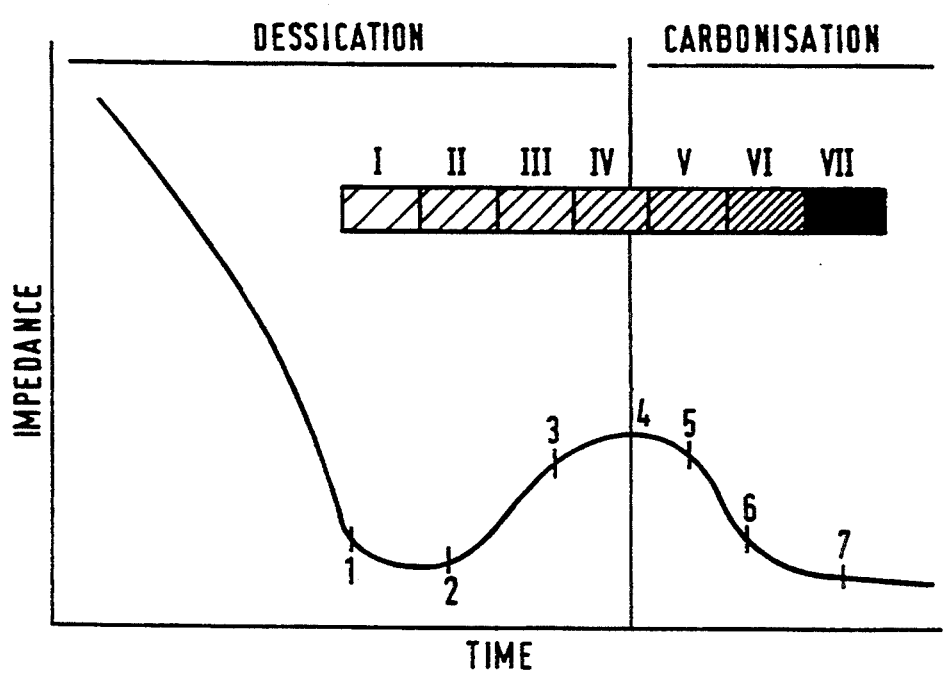
FIG. 2 is a graph showing the variation of resistance with time during a typical cauterisation operation.

It has been found that cauterisation of a blood vessel using a pair of forceps with active electrodes coupled across the output of an RF generator produces an resistance/time relationship of the form shown by the graph of FIG. 2. This relationship has an resistance dip followed by a peak. Firstly, during the desiccation phase, the resistance drops from an initial value dependent upon the size of the vessel being cauterised to an resistance minimum at which the colour of the vessel is off-white, as indicated by the left hand box I in the grey-scale bar of FIG. 2. As fluid continues to be boiled off the resistance rises to a maximum and the tissue becomes progressively darker. With increasing quantities of carbon being formed in the tissue, the resistance then begins to fall again to reach a minimum at the right hand side of the graph corresponding to a completely blackened blood vessel. It is this resistance variation that is monitored by the microcontroller 18 (FIG. 1) in order to determine the duration of power application from the power oscillator 16 to the forceps 10, the figures "1" to "7" representing 7 cautery levels set by the level setting device 22 of FIG. 1.

Figure 3:
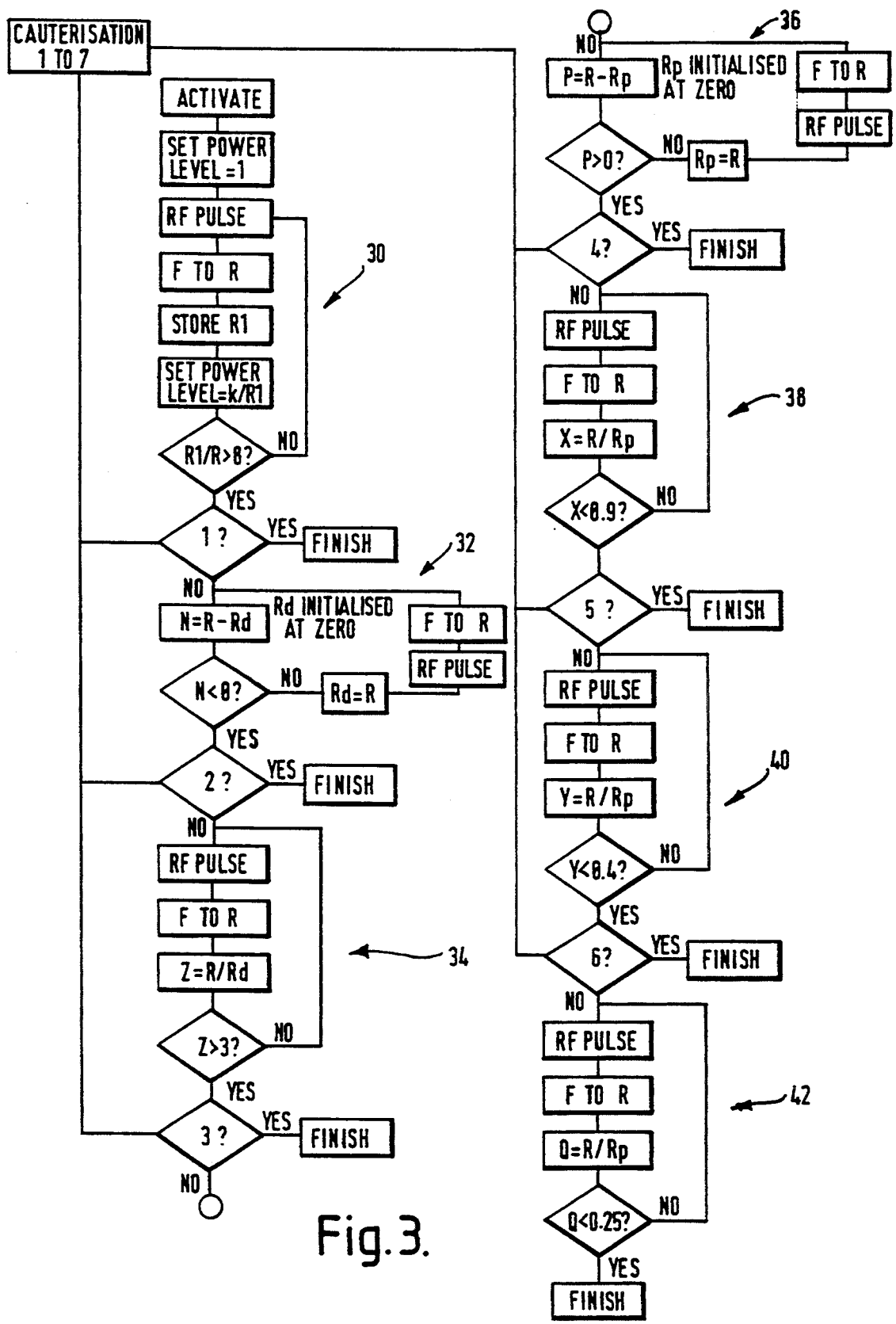
FIG. 3 is a flow chart showing the main steps in the operation of the microcontroller on the apparatus of FIG. 1.

As an illustration of a method of monitoring the resistance and controlling the power oscillator 12, a flow chart for a microprocessor program for the controller 18 is shown in FIG. 3.

Referring to FIG. 3 in combination with FIGS. 1 and 2, cautery is initiated by an "activate" instruction in the microcontroller 18, which causes the switched mode power supply to be set to an initial power level "1", where upon the switching device 16 is operated for a predetermined "on" time, so that an RF pulse is delivered to the forceps 10. During this pulse, the carrier cycles of the oscillator 12 are counted by the microcontroller and an F to R (frequency-to-resistance) conversion is performed using the look-up table in memory 20. This initial resistance value is stored as the value R1. Next, the power level is increased to a value determined by the expression k/R1 so that when the next RF pulse is transmitted, the power level is inversely proportional to the initially sensed resistance. At this point, the microcontroller 18 calculates the value of R1/R, in other words the ratio of the initial resistance to the most recently measured resistance, which initially for this first pulse will be equal to 1. If the calculated ratio is less than 8, the program loops back on loop 30 to transmit another RF pulse, this time with the power level set to k/R1. Another frequency-to-resistance conversion is performed, and this time the value stored is the value R which is again used in the calculation R1/R. The steps in loop 30 are repeated as many times as necessary until the calculation R1/R produces a ratio which is greater than 8. Referring to FIG. 2, it will be understood that the repeated transmission of these RF pulses to the forceps 10 produces desiccation of the blood vessel being cauterised so that the resistance follows a downward path until it is 1/8th of the initial value, as represented by point "1" towards the end of the initial slope.

At this point in the program, the cautery level setting device 22 is interrogated. If the setting is "1" cauterisation ceases. This corresponds to cauterisation to the off-white colour. If the cautery level setting is higher, the program passes to loop 32 which begins with setting a quantity N equal to R-Rd, Rd being initially zero. R is the last measured resistance value, which means that, initially, N equals R, which is greater than zero, so that Rd is then set to R, after a delay a pulse is transmitted, a new value of R is determined from the measured frequency, and the program returns to the beginning of loop 32. In the next cycle, therefore, N is obtained by subtracting the most recently measured value of R from the previous measured value. It will be seen that the program continues repeating loop 32 until the measured resistance begins to rise, corresponding to point "2" in FIG. 2. On exiting loop 32, the cautery level setting is again interrogated. If the setting is 2, cautery ceases with the colour of the blood vessel just beginning to darken as indicated by II in FIG. 2. If the level setting is greater than 2, the program progresses to loop 34 in which cauterising pulses are repeatedly transmitted until a ratio Z corresponding to the last mentioned resistance divided by the resistance measured in the last cycle of loop 32 exceeds 3, corresponding to point "3" in FIG. 2. Again, the cautery level setting is interrogated. If the setting is 3, cautery ceases. If not, the program progresses to loop 36.

In loop 36, as in loop 32, the program is looking for a change of sign of the resistance/time slope, only this time it is an resistance maximum which is being detected, rather than an resistance minimum. Thus, when the maximum, represented by the point "4" in FIG. 2 is reached, the cautery level setting is interrogated again, and cauterisation ceases if the cautery level is 4. If the cautery level is greater, cauterisation continues with loop 38.

This loop 38 is repeated until the resistance is less than 0.9 times the resistance at the maximum (point "4"), whereupon cauterisation ceases if the level setting is 5. If greater, a similar loop, loop 40 is executed repeatedly until the resistance is less than a value corresponding to 0.4 multiplied by the peak resistance value at point "4". This corresponds to cautery level setting 6. If a completely blackened blood vessel is required, the program executes the final loop, loop 42 which is exited when the resistance value is less than one quarter of the resistance value at point "4".

The flow chart at FIG. 3 forms the basis of the operation of the microcontroller 18. However, additional sophistication can be employed to provide alternative escapes to the loops. Thus for example, the software may include additional loop statements based on a power x time integral. It will be noted also that ratiometric calculations are used only outside the dip and peak, identification of the dip and peak being given priority in determining the extent of cauterisation.

In general terms, low-range cautery can be achieved by detecting the dip in the curve of FIG. 2. Mid-range cautery is detected by sensing a peak following a dip, indicating ending of the desiccation phase and beginning of carbonisation. High-range cautery is performed by detecting a fall in resistance following the peak.

As will be appreciated from the description of the flow chart above, the initial load resistance is calculated and plotted by the microcontroller, and all subsequent resistance values are normalised with respect to the initial resistance. Resistance values are taken for each modulation pulse, and measured with respect to the initial value.

If the RF generator is battery powered, it is preferred that the average power is controlled by controlling the length if the "on" pulses at the expense of achieving an ideal crest factor.

In the preferred embodiment described above the application of cauterising RF power can be cut-off automatically by the generator when the end point is reached. In some applications, however, it is desirable, within the scope of the present invention, to provide for manual cut-off by the surgeon, in which case the generator can be configured to provide a termination signal in the form of a display indication or an audible indication as a warning at or shortly in advance of reaching a predetermined end point.

We claim:

1. Electrosurgical cauterising apparatus comprising a radio frequency generator having a pair of output terminals for the delivery of radio frequency power at an output carrier frequency to a bipolar electrosurgical cauterising tool, wherein the generator includes means for altering the output carrier frequency of the delivered radio frequency power according to an electrical resistance of tissue being cauterised by the tool during cautery, output carrier frequency monitoring means for sensing said tissue resistance, and control means operable to generate a cautery termination signal in response to the sensed tissue resistance having reached a predetermined end point value, the signal being generated for terminating the delivery of cauterising radio frequency power to the cauterising tool.

2. Apparatus according to claim 1, wherein the control means are operable to detect a minimum sensed tissue resistance following an initial stage of cautery during which the tissue resistance is falling and to generate the termination signal at least approximately at the time of reaching the minimum.

3. Apparatus according to claim 1, wherein the control means is operable to detect a maximum sensed tissue resistance following an initial stage of cautery during which the tissue resistance is falling and an intermediate stage of cautery during which the tissue resistance is rising, and to generate the termination signal at least approximately at the time of reaching the maximum.

4. Apparatus according to claim 1, wherein the control means are operable to detect an initial period of falling tissue resistance followed by an intermediate period of rising tissue resistance and to generate the termination signal when the sensed tissue resistance has reached a value during one or either of the said periods which value has a predetermined relationship with the sensed tissue resistance at the beginning of the relevant said period.

5. Apparatus according to claim 1, including a cautery level setting device and wherein the control means are operable to store an initial tissue resistance value sensed at the beginning of cautery, and to detect a minimum sensed tissue resistance following an initial stage of cautery during which the tissue resistance is falling and a maximum sensed tissue resistance following an intermediate stage of cautery during which the tissue resistance is rising, and wherein the control means are further operable to generate the termination signal at any of a plurality of predetermined tissue resistance values occurring at different times during the initial period, the intermediate period, and a final period of cautery according to the setting of the level setting device.

6. Apparatus according to claim 5, wherein the control means are arranged such that each of at least some of the tissue resistance values are predetermined by having a particular ratio with respect to the last preceding one of the initial resistance value, the minimum resistance and the maximum resistance.

7. Apparatus according to claim 1, wherein the generator includes a switching device coupled to the control means and operable to stop delivery of radio frequency power in response to the termination signal.

8. Apparatus according to claim 1, wherein the generator includes a power control circuit coupled to the control means, and the control means are operable to feed a power setting signal to the power control circuit to set the output power of the generator according to an initial sensed tissue resistance.

9. Apparatus according to claim 8, wherein the control means are operable to feed a further power setting signal to the power control circuit when the sensed tissue resistance approaches the predetermined end point value in order to reduce the output power of the generator until the end point value is reached.

10. Apparatus according to claim 1, wherein the generator includes a power oscillator coupled to the output terminals and having an automatic output impedance adjusting circuit operable to alter the oscillator carrier frequency according to load resistance, and wherein the sensing means comprise a frequency counter.

11. Apparatus according to claim 10, wherein the control means comprise a microprocessor and a memory for storing a table allowing conversion of frequency counter values to tissue resistance values.

12. Apparatus according to claim 10, wherein carrier frequency is in the range of from 300 kHz to 5 MHz.

13. Apparatus according to claim 1, further comprising a surgical tool having a pair of cauterising electrodes, each electrode connected to a respective one of the output terminals of the generator.

14. Apparatus according to claim 13, wherein the surgical tool is a pair of forceps.

15. A method of operating electrosurgical cauterising apparatus having a radio frequency generator and a bipolar cauterising tool with cauterising electrodes coupled to the generator, comprising the steps of applying radio frequency power having an output carrier frequency to the electrodes, automatically altering the output carrier frequency of the applied radio frequency power according to an electrical resistance of tissue being cauterised between the electrodes during cautery, monitoring said output carrier frequency as a means of sensing said tissue resistance, generating a cautery termination signal in response to the sensed tissue resistance having reached a predetermined end point value, and ceasing application of radio frequency power.

16. A method according to claim 15, wherein the radio frequency power is applied as a stream of carrier pulses and wherein said tissue resistance is repeatedly sensed.

17. A method according to claim 15, including detecting a minimum sensed tissue resistance following an initial stage of cautery during which the tissue resistance is falling, and a maximum sensed tissue resistance following an intermediate stage of cautery during which the tissue resistance is rising, and generating the termination signal at least approximately when one of the said minimum and maximum is reached.

18. A method according to claim 15, including monitoring the sensed tissue resistance during at least one of initial, intermediate and final stages of cautery associated respectively with rising, falling and rising tissue resistance, storing tissue resistance values corresponding to the commencement of at least one of the said stages of cautery, and generating the termination signal when the sensed tissue resistance value has reached a predetermined relationship during a selected one of the said cautery stages with respect to the stored resistance value corresponding to the commencement of the selected stage.

19. A method according to claim 15, wherein the termination signal is generated in response to the sensed tissue resistance reaching a predetermined point on a resistance versus time curve characteristic of tissue cauterisation.

* * * * *